United States Patent
Yetter et al.

(10) Patent No.: US 8,007,288 B2
(45) Date of Patent: Aug. 30, 2011

(54) APPARATUS FOR CONNECTING A MULTI-CONDUCTOR CABLE TO A PIN GRID ARRAY CONNECTOR

(75) Inventors: Kelley E. Yetter, Lewistown, PA (US); Anand Desai, Lewistown, PA (US); John Pyle, Lewistown, PA (US); Jae Choi, Lewistown, PA (US)

(73) Assignee: GE Inspection Technologies, LP., Lewistown, PA (US)

( * ) Notice: Subject to any disclaimer, the term of this patent is extended or adjusted under 35 U.S.C. 154(b) by 0 days.

(21) Appl. No.: 12/566,923

(22) Filed: Sep. 25, 2009

(65) Prior Publication Data
US 2011/0076863 A1     Mar. 31, 2011

(51) Int. Cl.
*H01R 12/00*     (2006.01)
(52) U.S. Cl. .......................................... 439/71
(58) Field of Classification Search ............ 439/71, 439/77, 66, 67, 74; 257/737; 29/837, 760; 174/260
See application file for complete search history.

(56) References Cited

U.S. PATENT DOCUMENTS

| | | | |
|---|---|---|---|
| 5,038,467 A | 8/1991 | Murphy | |
| 5,313,021 A | 5/1994 | Sajja et al. | |
| 5,702,255 A | 12/1997 | Murphy et al. | |
| 5,813,881 A * | 9/1998 | Nathan et al. | 439/516 |
| 5,850,691 A | 12/1998 | Bell | |
| 7,005,742 B2 | 2/2006 | Hodson | |
| 7,438,581 B1 | 10/2008 | Jeon | |
| 2005/0245137 A1* | 11/2005 | Park et al. | 439/637 |
| 2009/0167287 A1* | 7/2009 | Van Meijl et al. | 324/66 |

* cited by examiner

*Primary Examiner* — Alexander Gilman
(74) *Attorney, Agent, or Firm* — Mark A. Conklin; Global Patent Operation

(57) ABSTRACT

An apparatus for connecting a multi-conductor cable of a first device to a pin grid array connector of a second device, wherein said apparatus comprises a first printed circuit board (PCB) for terminating the conductors of the cable, which are connected to a first PCB surface mounted connector mounted on the first PCB. The first PCB surface mounted connector is mated with a second PCB surface mounted connector mounted on a second PCB, on which a PCB surface mounted socket grid array is also mounted for mating to the pin grid array connector of the second device. This apparatus allows the same (i.e., standardized) multi-conductor cable with the same first PCB and the same first PCB surface mounted connector to be used regardless of what style connector is used by the second device.

8 Claims, 2 Drawing Sheets

APPARATUS FOR CONNECTING A MULTI-CONDUCTOR CABLE TO A PIN GRID ARRAY CONNECTOR

BACKGROUND OF THE INVENTION

This invention relates generally to an apparatus for connecting a multi-conductor cable to a pin grid array connector.

Electronic devices are often connected to other electronic devices by the use of one or more cables and connectors. In many such cases, the connectors, cables, and devices are standardized for universal type connections. For instance, a computer monitor having a standardized VGA connector can be connected to a personal computer having a standardized VGA connector by a standardized cable with standardized mating VGA connectors on both ends. Given this standardization, most any monitor can connect to most any personal computer as long as both were built within a certain time range because all or almost all commonplace varieties of personal computers and monitors built in the same approximate time period include standardized VGA connectors.

On the other hand, specialty electronic devices (e.g., driving electronics for testing devices such as phased array ultrasonic instrumentation) available from different manufacturers often have different types of connectors to connect to corresponding electronic devices. For example, a testing device available from one manufacturer can be operated or controlled through a multi-conductor cable (e.g., 16, 32, 64, or 128 conductors) extending from the testing device to a number of different possible driving electronic devices, each built by a different manufacturer and each using different types of connectors for connecting to the multi-conductor cable. With no accepted standardization of connectors for these specialized devices (i.e., driving electronics devices), multi-conductor cables linking the driving electronic device to the testing device must be custom-built to accommodate the particular connector on the driving electronic device. The cables can be micro coaxial, and run lengths up to and exceeding 50 meters.

For example, a multi-conductor cable extending from a particular testing device is typically terminated by soldering each conductor onto one or more cable terminating printed circuit boards (PCBs), each of which also has a cable terminating connector for mating with the driving electronics device. Each cable terminating PCB can have circuitry for connecting a particular conductor from the multi-conductor cable to a particular electrical contact of the cable terminating connector. The type of cable terminating connector can be selected such that it mates directly with the type of connector of the driving electronic device. However, this requirement that the cable terminating connector directly mate with various types of driving electronic device connectors eliminates the possibility of creating a standardized multi-conductor cable extending from a particular testing device, since each multi-conductor cable-to-driving electronics connector interface must be customized based on the different types of connectors used for the driving electronic devices (e.g., must terminate the multi-conductor cable with different types of cable terminating connectors depending on the connectors of the driving electronics devices).

Included in these different types of connectors used for the driving electronic devices are at least two general categories: (i) connectors that can directly mate with a PCB surface mounted connector, and (ii) connectors that have a pin grid array that cannot directly mate with a PCB surface mounted connector.

As for the driving electronics device connectors that can directly mate with a PCB surface mounted connector, there are several different types (e.g., type X, Y, or Z) that can interface with a single type of cable terminating connector (e.g., type A) through the use of PCBs, allowing for the use of a standardized multi-conductor cable (i.e., type of cable terminating connector (e.g., type A)) is not chosen based on the particular type of driving electronics device PCB surface mounted connector (e.g., type X, Y, or Z)). For example, the multi-conductor cable extending from a particular testing device can be terminated by soldering each conductor onto one or more cable terminating PCBs, each of which has a type A cable terminating PCB surface mounted connector. Each type A cable terminating PCB can have circuitry for connecting a particular conductor from the multi-conductor cable to a particular electrical contact of the type A cable terminating PCB surface mounted connector.

Each type A cable terminating PCB surface mounted connector can then be connected to a mating type A connector interfacing PCB surface mounted connector mounted on another PCB referred to as a connector interfacing PCB. In addition to the type A cable terminating PCB surface mounted connector, each connector interfacing PCB also has a connector interfacing PCB surface mounted connector of a type that mates directly with the driving electronics connector (e.g., type X, Y, or Z). Each connector interfacing PCB can have circuitry for connecting a particular electrical contact from the type A connector interfacing PCB surface mounted connector to a particular electrical contact of the type X, Y, or Z connector interfacing PCB surface mounted connector. The type X, Y, or Z connector interfacing PCB surface mounted connector can then be connected to the mating type X, Y, or Z driving electronics connector. Using this design, the same multi-conductor cable using a type A cable terminating connector can be used for all of the different types (e.g., type X, Y, or Z) of the driving electronics device PCB surface mounted connectors by using different connector interfacing PCBs for the different types of driving electronics device PCB surface mounted connectors, without significantly increasing the amount of complicated, labor-intensive, time consuming, and costly hand wiring.

As for driving electronic device connectors that have a pin grid array (PGA) that cannot directly mate with a PCB surface mounted connector, those connectors cannot presently interface with a single type of cable terminating connector (e.g., type A) through the use of PCBs, and therefore do not allow for the use of a standardized multi-conductor cable. For example, the multi-conductor cable extending from a particular testing device can be terminated by soldering each conductor onto one or more cable terminating PCBs, each of which has a cable terminating connector that must be selected such that it mates directly with a row of pins in the PGA of the driving electronic device connector. Each cable terminating PCB can have circuitry for connecting a particular conductor from the multi-conductor cable to a particular electrical contact of the cable terminating connector, which is then mounted directly to the PGA connector of the driving electronics device. Accordingly, each different type of PGA driving electronic device connector requires a customized multi-conductor cable.

It would be advantageous to be able to use a standardized multi-conductor cable (i.e., type of cable terminating connector is not chosen based on the particular type of driving electronics device connector) regardless of whether the cable is connecting to a connector that can directly mate with a PCB surface mounted connector or a PGA connector that cannot directly mate with a PCB surface mounted connector.

BRIEF DESCRIPTION OF THE INVENTION

An apparatus for connecting a multi-conductor cable of a first device to a pin grid array connector of a second device is disclosed, wherein said apparatus comprises a first PCB for terminating the conductors of the cable which are connected to a first PCB surface mounted connector mounted on the first PCB. The first PCB surface mounted connector is mated with a second PCB surface mounted connector mounted on a second PCB, on which a PCB surface mounted socket grid array is also mounted for mating to the pin grid array connector of the second device. This apparatus allows the same (i.e., standardized) multi-conductor cable with the same first PCB and the same first PCB surface mounted connector to be used regardless of what style connector is used by the second device.

DETAILED DESCRIPTION OF THE INVENTION

Figure 1:
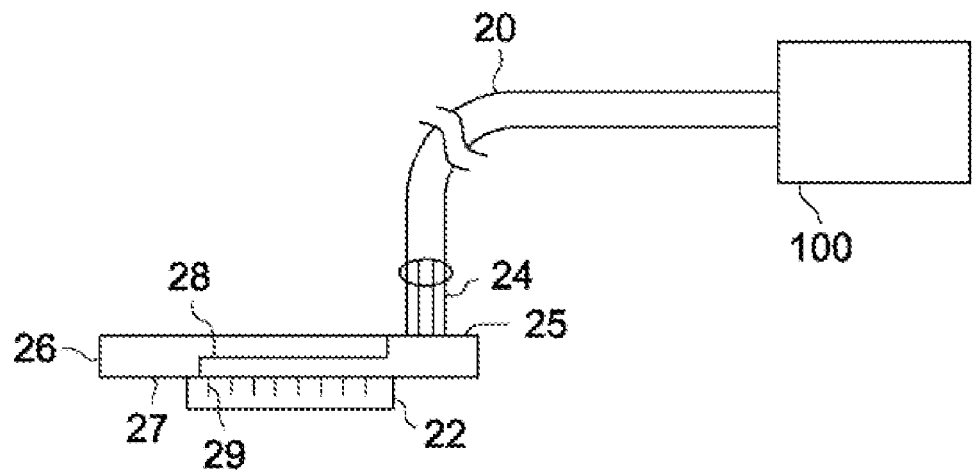
FIG. 1 illustrates one embodiment of an exemplary multi-conductor cable extending from a first electronic device and terminated on one or more cable terminating PCBs, each having one or more cable terminating PCB surface mounted connectors mounted to the PCBs.

FIG. 1 illustrates one embodiment of an exemplary multi-conductor cable 20 extending from a first electronic device 100 and terminated on one or more cable terminating PCBs 26, each having one or more cable terminating PCB surface mounted connectors 22 mounted to the PCBs 26. The number of cable terminating PCBs 26 and cable terminating PCB surface mounted connectors 22 can be determined by the number of required conductors in the multi-conductor cable 20. Each cable terminating PCB surface mounted connector 22 can be a low profile style in order to minimize the use of space extending perpendicularly from the cable terminating PCB 26. The individual conductors 24 of the multi-conductor cable 20 extending from the first electronic device 100 can be terminated by soldering each conductor 24 onto a first surface 25 of a cable terminating PCB 26, which has a cable terminating PCB surface mounted connector 22 on the second surface 27 of the cable terminating PCB 26. Each cable terminating PCB 26 can have circuits 28 to which a particular conductor 24 from the multi-conductor cable 20 is soldered and then connected to a particular electrical contact 29 of the cable terminating PCB surface mounted connector 22. The cable terminating PCB surface mounted connector 22 can be a male or female type.

Figure 2:
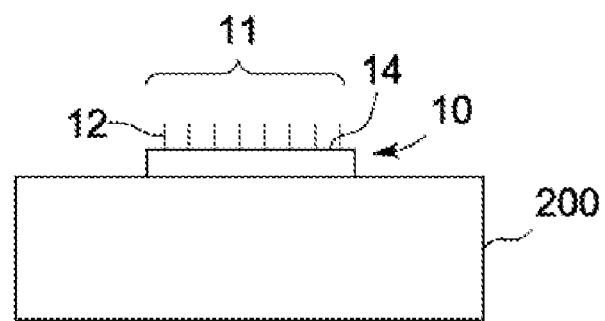
FIG. 2 illustrates one embodiment of an exemplary PGA connector of a second electronic device.

FIG. 2 illustrates one embodiment of an exemplary PGA connector 10 of a second electronic device 200. A PGA connector 10 can have a pin grid 11 with a plurality of electrical contacts in the form of pins 12. These pins 12 extend in a direction parallel to each other, perpendicularly from a first surface 14 of the PGA connector 10. The pins 12 can vary in number and be arranged in various geometries and configurations (e.g., certain number of rows and columns) to form a variety of pin grids 11. For example, the pins 12 for two different PGA connectors can be arranged with different quantities and center-to-center spacings (e.g., spaced 0.100 inches (2.54 mm) or 0.050 inches (1.27 mm)). The particular PGA connector 10 illustrated in FIG. 1 is referenced herein throughout to illustrate the present invention, which can be modified in order to accommodate various configurations and specifications of PGA connectors 10 different from the one illustrated herein.

Figure 3:
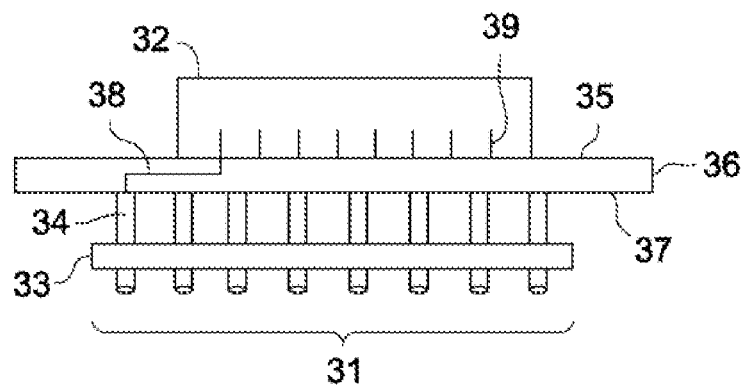
FIG. 3 illustrates one embodiment of an exemplary connector interfacing PCB having one or more connector interfacing PCB surface mounted connectors for mating with the cable terminating PCB surface mounted connectors and one or more connector interfacing PCB surface mounted socket grid arrays (SGAs) for mating with the PGA connector of the second electronic device.

FIG. 3 illustrates one embodiment of an exemplary connector interfacing PCB 36 having one or more connector interfacing PCB surface mounted connectors 32 mounted to a first surface 35 for mating with the cable terminating PCB surface mounted connectors 22, and one or more connector interfacing PCB surface mounted socket grid arrays 33 mounted to a second surface 37 for mating with the PGA connector 10 of the second electronic device 200. The number of connector interfacing PCBs 36, cable terminating PCB surface mounted connectors 32, and connector interfacing PCB surface mounted socket grid arrays 33 can be determined by the number of required conductors in the multi-conductor cable 20 or the number of pins 12 on the PGA connector 10. Each connector interfacing PCB surface mounted connector 32 can be a low profile style in order to minimize the use of space extending perpendicularly from the connector interfacing PCB 36. Each connector interfacing PCB surface mounted socket grid arrays 33 can have a socket grid 31 with a plurality of electrical contacts in the form of sockets 34, which have interior electrical contacts. These sockets 34 extend in a direction parallel to each other, perpendicularly from the second surface 37 of the connector interfacing PCB 36. The sockets 34 can vary in number, and be arranged in various geometries and configurations to form a variety of socket grids 31 to mate with the pin grids 11 of the PGA connector 10 of the second electronic device 200. The individual sockets 34 of the connector interfacing PCB surface mounted socket grid arrays 33 can be soldered onto the second surface 37 of a connector interfacing PCB 36, which has a connector interfacing PCB surface mounted connector 32 on the first surface 35 of the connector interfacing PCB 36. Furthermore, to provide extra support or adherence between the connector interfacing PCB surface mounted socket grid arrays 33 and the second surface 37, epoxy can be applied at the contact between the sockets 34 and second surface 37, or more extensively between the socket grid arrays 33 and the second surface 37. Extra support or adherence might be necessary, for instance, to accommodate any difference between the thermal expansion coefficients of the materials on either side of the union, including any solder used. When the coefficient of thermal expansion (CTE) of one part differs from the CTE of a part connected by solder, the two parts expand at different rates during heating, causing stress to the soldered joint. The application of an epoxy, such as an A stage or B stage epoxy, can provide extra support to the joint. This support can also provide protection against other physical stressors, including but not limited to vibration, impact, and other physical shock.

Each cable terminating PCB 36 can have circuits 38 to which a particular socket 34 of the connector interfacing PCB surface mounted socket grid array 33 is soldered and then connected to a particular electrical contact 39 of the connector interfacing PCB surface mounted connector 32. The connector interfacing PCB surface mounted connectors 32 can be a male or female type in order to mate with the particular configuration of the cable terminating PCB surface mounted connectors 22.

Figure 4:
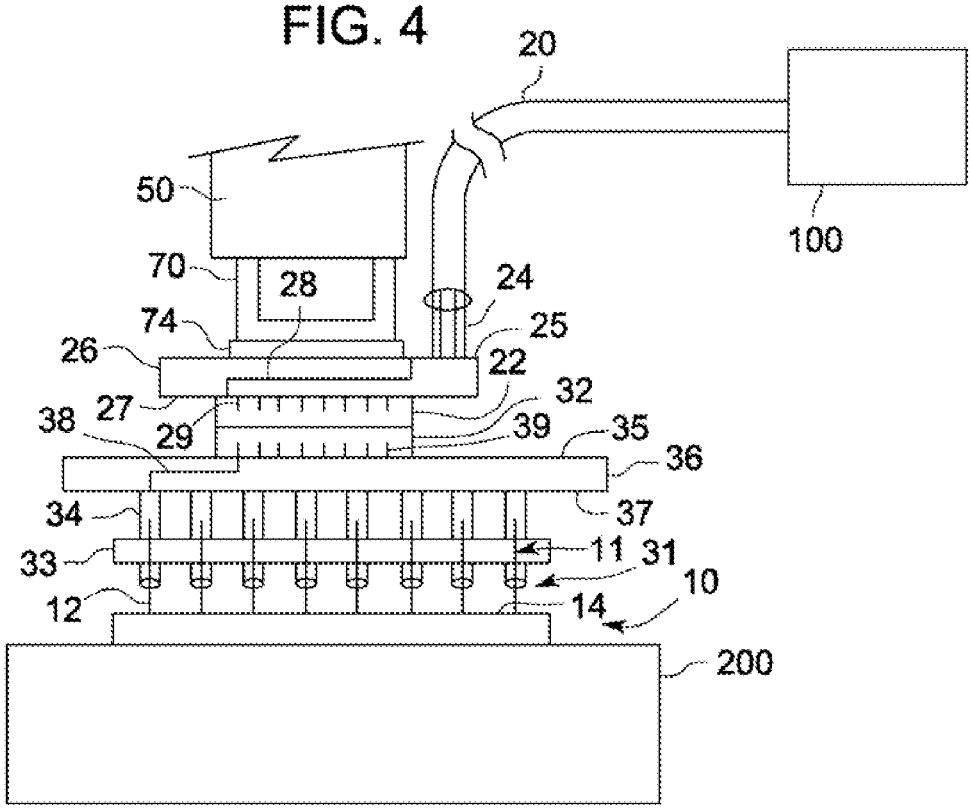
FIG. 4 illustrates one embodiment of the exemplary connector interfacing PCB interfacing the cable terminating PCB surface mounted connectors to the PGA connector of the second electronic device.

FIG. 4 illustrates one embodiment of the exemplary connector interfacing PCB 36 interfacing the cable terminating PCB surface mounted connectors 22 to the PGA connector 10 of the second electronic device 200 via the connectors and circuits on the connector interfacing PCB 36. As illustrated, the pins 12 of the PGA connector 10 of the second electronic device 200 are inserted into the sockets 34 of the connector interfacing PCB surface mounted socket grid array 33, which are connected to a particular electrical contact of the connector interfacing PCB surface mounted connector 32, which is mated with a particular electrical contact of the cable terminating PCB surface mounted connector 22, which is connected to a particular conductor 24 from the multi-conductor cable 20, which extends from the first electronic device 100. It can be seen from this assembly, that regardless of what style of connector is used for the second electronic device 200, the same (i.e., standardized) multi-conductor cable 20 with the same cable terminating PCB surface mounted connectors 22 can be used, since all that must be customized is the connector interfacing PCB 36.

In order to maintain the connections between the various connectors and PCBs, a support device 70 (e.g., a clamp or bracket) can be used as shown in FIG. 4. The support device 70 can be placed in position on top of each cable terminating PCB surface mounted connector 22 and fixed to a housing (not shown) or otherwise held firmly against each cable terminating PCB surface mounted connector 22. The support device 70 can be made of metal, plastic, or any semi-rigid or rigid material. For example, aluminum can be used based on its light weight and malleability. A pad 74 can be placed between the support device 70 and the top of each cable terminating PCB surface mounted connector 22. This pad 74 (e.g., a sponge, soft foam, or other cushioning material) can protect the electrical components from being damaged by contact or pressure against the bottom surface of the support device 70, which can be hard or abrasive.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for connecting a multi-conductor cable to a pin grid array connector comprising:
  a first printed circuit board comprising a first plurality of circuits connected to a plurality of conductors from said multi-conductor cable;
  a first printed circuit board surface mounted connector mounted to said first printed circuit board, wherein said first printed circuit board surface mounted connector comprises a first plurality of electrical contacts connected to said first plurality of circuits and said plurality of conductors from said multi-conductor cable via said first plurality of circuits;
  a second printed circuit board comprising a second plurality of circuits;
  a second printed circuit board surface mounted connector mounted to said second printed circuit board and mated to said first printed circuit board surface mounted connector, wherein said second printed circuit board surface mounted connector comprises a second plurality of electrical contacts mated to said first plurality of electrical contacts and connected to said second plurality of circuits; and
  a printed circuit board surface mounted socket grid array mounted to said second printed circuit board for mating to said pin grid array connector, wherein said printed circuit board surface mounted socket grid array comprises a plurality of sockets connected to said second plurality of circuits and said second plurality of electrical contacts via said second plurality of circuits.

2. The apparatus of claim 1, wherein said first plurality of circuits are connected to said plurality of conductors from said multi-conductor cable by soldering said plurality of conductors to said first plurality of circuits.

3. The apparatus of claim 1, wherein said second plurality of circuits are connected to said plurality of sockets by soldering said plurality of sockets to said second plurality of circuits.

4. The apparatus of claim 3 further comprising epoxy between said printed circuit board surface mounted socket grid array and second printed circuit board.

5. The apparatus of claim 1 further comprising:
  a housing; and
  a support device fixed to said housing and positioned adjacent to and coupled with said first printed circuit board surface mounted connector.

6. The apparatus of claim 5 further comprising a pad between said support device and said first printed circuit board surface mounted connector.

7. The apparatus of claim 5, wherein said support device is a clamp or a bracket.

8. The apparatus of claim 1, wherein said first printed circuit board surface mounted connector and said second printed circuit board surface mounted connector are low profile style connectors.

* * * * *